US012661025B2

(12) United States Patent
Jamrozy et al.

(10) Patent No.: US 12,661,025 B2
(45) Date of Patent: Jun. 23, 2026

(54) METHOD AND DEVICE FOR MULTIDIMENSIONAL ANALYSIS OF THE DYNAMICS OF CARDIAC ACTIVITY

(71) Applicant: EFM S.A., Bialystok (PL)

(72) Inventors: Milosz Jamrozy, Marianow (PL);
Tomasz Leyko, Warsaw (PL);
Aleksander Cudny, Warsaw (PL)

(73) Assignee: EFM S.A., Bialystok (PL)

( * ) Notice: Subject to any disclaimer, the term of this patent is extended or adjusted under 35 U.S.C. 154(b) by 371 days.

(21) Appl. No.: 18/001,101

(22) PCT Filed: Jun. 8, 2021

(86) PCT No.: PCT/EP2021/065371
§ 371 (c)(1),
(2) Date: Dec. 8, 2022

(87) PCT Pub. No.: WO2021/250048
PCT Pub. Date: Dec. 16, 2021

(65) Prior Publication Data
US 2023/0210393 A1 Jul. 6, 2023

(30) Foreign Application Priority Data

| | | |
|---|---|---|
| Jun. 8, 2020 | (EP) | ..................................... 20178686 |
| Jun. 8, 2020 | (PL) | ........................................ 434233 |
| Jun. 9, 2020 | (IT) | ......................... 20202000013756 |

(51) Int. Cl.
*A61B 5/0245* (2006.01)
*A61B 5/318* (2021.01)

(52) U.S. Cl.
CPC ............ *A61B 5/0245* (2013.01); *A61B 5/318* (2021.01)

(58) Field of Classification Search
CPC ..... A61B 5/0245; A61B 5/318; A61B 5/0535; A61B 5/333; A61B 5/341; A61B 5/0285; A61B 5/02125; A61B 5/33
See application file for complete search history.

(56) References Cited

U.S. PATENT DOCUMENTS

| | | | |
|---|---|---|---|
| 4,106,495 A | 8/1978 | Kennedy | |
| 2009/0262109 A1* | 10/2009 | Markowitz | ............ A61B 34/20 |
| | | | 345/419 |

(Continued)

FOREIGN PATENT DOCUMENTS

| | | |
|---|---|---|
| CN | 2178501 | 10/1994 |
| DE | 2620285 B1 | 9/1977 |

OTHER PUBLICATIONS https://www.bem.fi/book/book.pdf (Year: 1995).*

(Continued)

*Primary Examiner* — Carl H Layno
*Assistant Examiner* — Dhrasti Snehal Dalal
(74) *Attorney, Agent, or Firm* — Ziegler IP Law Group, LLC

(57) ABSTRACT

The present disclosure relates to a method for measuring multidimensional dynamics of cardiac activity comprising simultaneous measurement of
three dimensional ECG,
three dimensional impedance rheometry,
tissue motion, wherein the tissue motion measurement is performed with a sensor placed outside the patient body selected from among sensors including: membrane, auscultation funnel, accelerometer, microphone, piezoelectric sensor,
wherein the impedance rheometry measurement includes simultaneous generation of applied current of different frequencies for three orthogonal axes and an impedance measurement for the same or other three orthogonal axes, and (Continued)

wherein the impedance rheometry measurement and the ECG measurement are carried out for the same three orthogonal axes.

The present disclosure further relates to a device for implementation of the method.

7 Claims, 3 Drawing Sheets

(56) References Cited

U.S. PATENT DOCUMENTS

| | | | | |
|---|---|---|---|---|
| 2012/0296227 A1* | 11/2012 | Chen | ...................... | A61B 5/349 |
| | | | | 600/509 |
| 2015/0157220 A1* | 6/2015 | Fish | ..................... | A61B 5/0002 |
| | | | | 600/595 |

| | | | | |
|---|---|---|---|---|
| 2019/0133516 A1* | 5/2019 | Banet | ...................... | A61M 1/14 |
| 2019/0282821 A1* | 9/2019 | Masuda | ............... | A61N 1/0476 |
| 2020/0037907 A1* | 2/2020 | van Dam | ............... | A61B 5/341 |

OTHER PUBLICATIONS

Hanne et al, "An Unobtrusive Wearable Device for Ambulatory Monitoring of Pulse Transit Time to Estimate Central Blood Pressure" Proceedings of the 9th International Joint Conference on Biomedical Engineering systems and Technologies, pp. 179-186, XP055639045, DOI: 10.5220/0005701401790186, ISBN: 978-989-7581-70-0, Feb. 23, 2016.

International Search Report, Application No. PCT/EP2021/065371, Mailed Aug. 5, 2021, 3 pages.

Parastoo et al, "Comparison of Different Methods for Estimating Cardiac Timings: A Comprehensive Multimodal Echocardiography Investigation", Frontiers in Physiology, vol. 10, XP055770838, DOI: 10.3389/fphys.2019.01057, Aug. 22, 2019.

* cited by examiner

METHOD AND DEVICE FOR MULTIDIMENSIONAL ANALYSIS OF THE DYNAMICS OF CARDIAC ACTIVITY

FIELD

The aspects of the present disclosure relate to a method for measuring energy of cardiac activity and time course of cardiac contraction by measuring impedances and voltages, and a device for implementing this method.

BRIEF DESCRIPTION OF RELATED DEVELOPMENTS

There are known devices for monitoring various parameters of cardiac activity including for instance blood pressure, heart rate (HR) using ECG, stroke volume (minute volume) using cardiac impedance, or haemoglobin oxygen saturation ($SpO_2$) using pulse oximeter. These are not, however, devices which are dedicated to searching for dependencies between the time course of cardiac contraction and the stimulation and result of the contraction. The contraction time course can be observed using methods such as: echocardiography, magnetic resonance, computer tomography, nuclear medicine methods. Each of them requires an expensive equipment, trained personnel and experience. There is currently no known device on the market which is used for searching a relationship between the aforementioned phenomena.

There is also no known device that would simultaneously perform vectorcardiography and three-dimensional cardiac impedance. A 3D-rheometry measurement with classical electrocardiography is used in systems for navigation during heart ablation procedures in arrhythmia treatment. In this case, the real and imaginary parts of the impedance are not measured—what is only measured is the resistance, and additionally, the measurement is performed between a tool in the human body and the electrodes stuck to the body. The cardiac activity related changes in chest impedance represent a disturbance in this measurement, an expected information is the position of the tool with respect to the measuring electrodes—that's why a heart rate synchronous averaging is used to stabilize the reconstructed images.

US20110295127A discloses a device and method for vibro-acoustic detection of cardiac arrhythmia. Measurements of vibrations are performed and based on the frequency and amplitude changes it is possible to determine if and which disturbances occur. The dynamics of cardiac activity is nonlinear because of many independent systems of cardiac rhythm regulation. For that reason, a frequency analysis, which requires linearity, does not fall within the scope of the disclosed embodiments.

US20150374256A1 discloses a device which can measure the dynamics of cardiac activity and examine the flow of fluids. The measurement is performed by using leads on the patient's body, where also current and voltage, pressure and vibrations are probed. The dynamics which are determined by the disclosed device relate to blood—the detected parameters are hemodynamic parameters, and the determination thereof consists in applying a model allowing for estimation of the blood motion and in determining, for instance, the cardiac stroke volume. The solution disclosed herein is not limited to the assessment of hemodynamics.

US2009/262109 discloses a system and a method of mapping the patient body in order to navigate the device inserted inside the patient's body. Among other elements, the system includes means for measuring of impedance in three orthogonal axes (with different current frequencies on each axe) as well as separate means for ordinary ECG measurements using three, electrodes separate front the ones used in case impedance measurements. The device inserted in the patient's body is a catheter having a balloon for measuring blood pressure and reference electrode used to estimate the position of the catheter based on measured impedance values.

Publication of Prastoo D. et. al. (*Comparison of Different Methods for Estimating Cardiac Timings: A comprehensive Multimodal Echocardiography Investigation*, Frontiers in Physiology, vol. 10, 22 Aug. 2019) discloses a method involving simultaneous ECG, ICG and PCG measurements. However, no information is disclosed relating to three-dimensional measurements or using electrodes located on three orthogonal axes.

CN2178501 discloses a impedance measurement method using three orthogonal axes. However CN2178501 is silent on using various current frequencies on each exe as well as on combining such measurement with three dimensional ECG or tissue movement measurement.

The solution disclosed herein allows for preliminary assessment of cardiac activity and qualification for an expensive image diagnostics based on a 3D-measurement of ECG signal, 3D-measurement of impedance rheometry, and, preferably, acoustic, vibrational or ultrasonic signals.

The measurement apparatus described below will enable an advanced analysis of signals to allow differentiation of heart diseases by evaluation of the mode of heart motion in the chest. It will allow for non-invasive diagnostics of various heart diseases, which can additionally be automated and available in every clinic.

SUMMARY

The disclosed embodiments relates to a method for measuring multidimensional dynamics of cardiac activity comprising simultaneous measurement of three dimensional ECG and three dimensional impedance rheometry, wherein the impedance rheometry measurement comprises simultaneous generation of applied current of different frequencies for three orthogonal axes and an impedance measurement for the same or other three orthogonal axes and wherein the impedance rheometry measurement and the ECG measurement are carried out for the same three orthogonal axes.

The method comprises a tissue motion measurement, simultaneous with the ECG measurement and the impedance rheometry measurement. The measurement applies in particular to tissues that move in the chest, such as contractile tissues (muscles) and those that are moved by the contractile tissues (e.g. lung tissue).

The tissue motion measurement is performed with a sensor placed outside the patient body selected from among sensors including: membrane, auscultation funnel, accelerometer, microphone, piezoelectric sensor.

According to the present disclosure, the term "outside the patient body" used with respect to tissue motion measurements means that the tissue measurement sensor is used in substantially non-invasive manner, preferably the sensor is placed on the patient's skin.

Preferably, the impedance rheometry measurement is performed for three orthogonal axes whose intersection is in the heart area.

Preferably, the ECG measurement and/or the impedance rheometry measurement and/or the generation of applied current are carried out using electrodes in Frank configuration or in Leyko-Jamroży configuration, where the Z axis is determined by the first electrode located in the right supraclavicular fossa and the second electrode located in the position of the apex beat, the X axis is determined by the third electrode located at Erb's point (the third or fourth intercostal space, at the left edge of the sternum) and the fourth electrode in the right posterior axillary line at its intersection with the line perpendicular to the Z axis and passing through the first electrode of the X axis, the Y axis is determined by the fifth electrode located in the left posterior axillary line at the height of the third or fourth intercostal space and the sixth electrode on the surface of the body at the exit point of the line passing through the first point of the Y axis and the point intersecting the X and Z axes.

Preferably, the measurements are carried out using one time base.

Preferably, the measurement step is followed by a step of calculating currents, energy and work related to myocardium activity based on the measurement data.

Preferably, the method further comprises a step of assessing the dynamics of changes in the signal waveforms.

The disclosed embodiments relate also to a device for multidimensional analysis of the dynamics of cardiac activity adapted for simultaneous ECG and impedance rheometry measurement, comprising a three dimensional ECG measurement system, a three dimensional impedance rheometry measurement system, a system for generation of applied currents, an electrode system comprising electrodes arranged on three orthogonal axes, comprising separate electrodes of the ECG measurement system, the impedance rheometry measurement system and the system for generation of applied currents, wherein the ECG measurement system, the impedance rheometry measurement system and the system for generation of applied currents are adapted for simultaneous measurement in three orthogonal axes, and further the frequency of the applied current is different for each of the three orthogonal axes, and at least one tissue motion sensor adapted to be disposed outside of the patient body, selected from among sensors including: membrane, auscultation funnel, accelerometer, microphone, piezoelectric sensor.

Preferably, all systems of the device have a common time base.

Preferably, the device comprises an interface for data transfer.

Preferably, the device comprises a pulse oximetry device with PTT measurement.

BRIEF DESCRIPTION OF THE DRAWINGS

The disclosed embodiments will be now explained in detail, in an embodiment, with reference to accompanying Figures, wherein.

DESCRIPTION OF THE DISCLOSED EMBODIMENTS

The device is part of a system that receives signals and analyzes them. The task of the system is to extract information on generally understood dynamics of cardiac activity—not limited to hemodynamics (blood motion in the heart and vessels), but covering the motion of cardiac tissues in the chest, assessment of energy generated by the heart through estimation from current and impedance measurements. The task of the system is to obtain information on the phenomena related to the electrical aspect of cardiac activity in three-dimensional terms (ECG and 3D-cardioimpedance), to obtain holistic information about the motion of cardiac tissues (microphone, accelerometer, ultrasonic measurement), and possibly also about the condition of vessels, the vascular resistance and the pulse wave (as a PTT measurement). Collecting this information synchronously allows for analyzing the relationships between individual contractions and studying the dynamics of various processes. Due to the presence of several regulation systems of (heart rate) stimulation, the cardiac activity is non-linear and the stability of the activity observed in healthy condition, when measured at rest, disappears in sick patients.

Along with the disease and the resulting chaotic activity of the overloaded heart, we observe a very rich and complex dynamics of motion of cardiac tissues, a decrease in the efficiency of heart as a pump and an increase in the energy input needed to maintain the required flows in the body. All these aspects can be measured with the solution according to the present disclosed embodiments.

The device for multidimensional analysis of the dynamics of cardiac activity according to the present disclosed embodiments comprises leads for the three dimensional ECG measurement and leads for three dimensional impedance rheometry in three orthogonal axes. The leads are attached to the body with electrodes. The lead system used for impedance rheometry has preferably a centre in the heart area. The device comprises three electrode signal measuring systems, three systems for generation of applied currents and at least one tissue motion sensor. Preferably, the device comprises a communication interface with the user. The signal receiving systems and the systems for generation of applied currents are configured for simultaneous measurement in three orthogonal axes. The frequency of the applied current is different for each of the three orthogonal axes.

Correct data collection must meet the following conditions:

The impedance measurement must be carried out for three orthogonal axes for three different frequencies. The measurement cannot be performed sequentially, and further the electrode system may be different from the lead system (only the orthogonality of the axes is important).

The impedance and voltage measurements need not be carried out in the same axes.

All measurements must be made simultaneously, sequential measurements for subsequent axes are not allowed.

Figure 2:
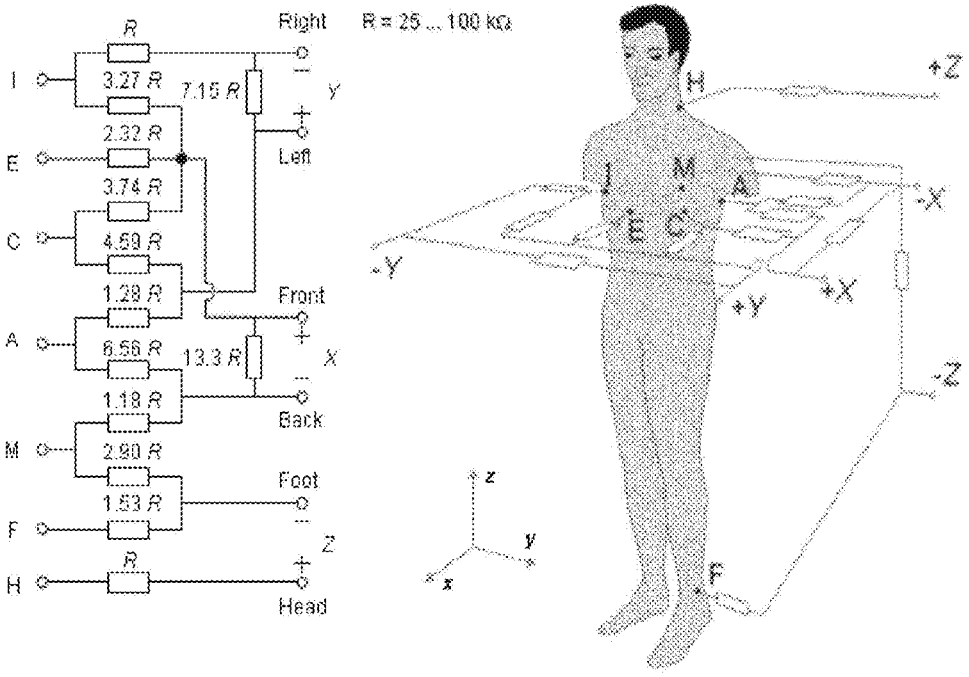
FIG. 2 shows the Frank lead configuration.

The real and imaginary parts of impedance are measured simultaneously in each axis, where the ECG is measured. As shown in FIG. 2, the measurement is carried out in three orthogonal axes: the X axis (measurement points E and M), the Y axis (measurement points I and A), the Z axis (measurement points F and H). Due to this measurement, it will be possible to use information about the tissue resistance and voltage changes in perpendicular axes. This enables estimation of currents, energy and work related to myocardium activity.

Figure 1:
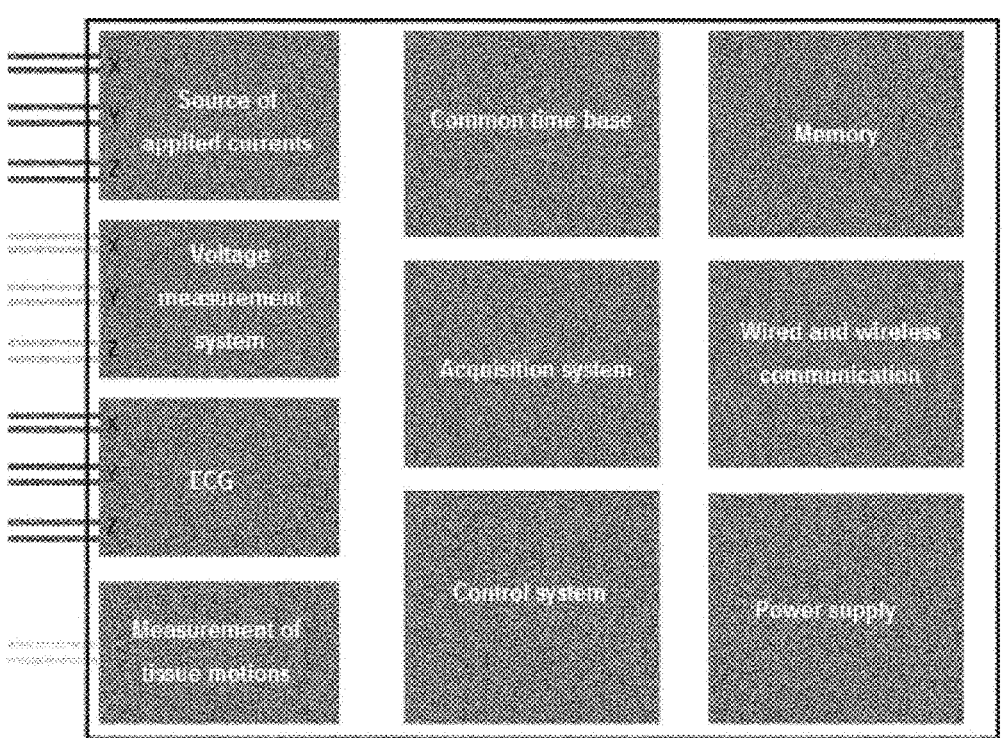
FIG. 1 shows schematically components of the device according to the disclosed embodiments.

Functionally, the device according to the embodiment can be divided into several modules, i.e. measuring, communication, control, memory, power supply, information display and user communication module, as shown in FIG. 1. It should be emphasized that the information display and user communication module or the communication module are optional. Small, portable devices will be mainly used to record and save data, while in the case of testing it may turn out that further data transmission is not necessary.

The device is designed to perform synchronously (preferably using one time base) measurement of 3 orthogonal ECG leads, 3 orthogonal reactance and resistance measurements, and at least one measurement related to the tissue motion in chest, and preferably other additional signals are also measured. Such a measurement of tissue motion may be, for instance, a measurement of an acoustic signal with a diaphragm or auscultation funnel, a vibration signal (measured by any method), a Doppler signal measured by pulse or continuous wave method, with one or multiple transducers.

An important difference between the measurements with the present device and with devices enabling measurements of similar signals, is that the present device does not use models enabling reference to physiology or anatomy (e.g., by setting up a model allowing for estimation of the stroke volume, tissue hydration from a rheometric signal, or mapping information on a reconstructed anatomical model—a tissue Doppler). The essence of the recording provided by the present device is that the measured physical properties are simultaneously recorded using transducers—for instance voltage in orthogonal leads expressed in mV, resistance expressed in ohms, pressure changes in the auscultation funnel expressed, for instance, in pascals, etc. Therefore, the arrangement of electrodes differs from typical applications, which due to the models behind them allows for diagnosing—for instance, the use of Wilson leads in ECG enables the assessment of left ventricular hypertrophy based on meeting the criteria for voltages in individual channels.

Due to the fact that the applied currents in each of the three orthogonal axes will flow simultaneously, different frequencies must be used for each channel. This means that the measured signal in each of the three receiving systems will represent the superposition of three frequencies. To perform a high quality measurement, special signal processing path and synchronization must be used which prevents the use of 3 independent rheometers even if they can be tuned to different frequencies.

The collected signals are subsequently used for analysis with the aim to assess the dynamics of cardiac activity (not to be confused with the hemodynamic assessment, which describes the dynamics of the blood flow). To this end, the whole set of collected signals is assessed, including electrical (changes of voltage and impedance in chest) and mechanical (tissue motion) phenomena. Together, they will set up a multidimensional picture of phenomena over time, the variability of which is studied and evaluated.

The device preferably uses an electrode system that forms a Frank lead system or a Leyko-Jamroży lead system, where the Z axis is determined by the first electrode located in the right supraclavicular fossa and the second electrode located in the position of the apex beat, the X axis is determined by the third electrode located at Erb's point (the third or fourth intercostal space, at the left edge of the sternum) and the fourth electrode in the right posterior axillary line at its intersection with the line perpendicular to the Z axis and passing through the first electrode of the X axis, the Y axis is determined by the fifth electrode located in the left posterior axillary line at the height of the third or fourth intercostal space and the sixth electrode on the surface of the body at the exit point of the line passing through the first point of the Y axis and the point intersecting the X and Z axes.

The motion sensor should be located in the subsequent intercostal space above the position of the apex beat.

The set of three electrodes is placed on one triple adhesive tape. The centre of the orthogonal coordinate system in the heart area.

Preferably, the device has a lead system for ECG measurement and a lead system for impedance rheometry, which systems have their centres essentially in the same place, and even more preferably the lead systems are the same for ECG and impedance rheometry measurements. In the most favourable variant, the impedance and voltage measurements are performed in the same axes.

Preferably, the leads are connected to the body through triple electrodes.

The measuring system in the rheometry measurement and the system for generation of applied currents can use separate or the same electrodes.

Preferably, all device systems have a common time base. It is possible to synchronize systems without a common time base, an easier and more practical synchronization can be, however, achieved through a common time base.

The method of measuring multidimensional dynamics of cardiac activity according to the disclosed embodiments comprises steps of attaching the lead electrodes to the body, simultaneously measuring ECG and impedance rheometry in three orthogonal axes by simultaneously generating applied current with different frequencies for each axis and measuring voltages between electrodes and calculating currents, energy and work related to myocardial activity based on the measurement data. Preferably, the device or the data analyzing system uses the data to assess the dynamics of signal waveform changes.

The device can also be equipped with an accelerometer and/or pulse oximetry device with PTT (Pulse Transit Time) measurement.

The device may also have a module for multi-channel measurement of tissue motion with continuous wave or pulse Doppler method (similar to the method used in CTG or tissue Doppler in echocardiography).

The device may be equipped with an additional accelerometer for measuring the patient's physical activity.

The device can be implemented in a stationary or portable form. It can be integrated into one device with other peripherals (screens, touch screens, keyboards, mice, glasses for virtual reality, etc., on a mobile supporting structure) or consist of components connected in various ways (e.g., the main unit and cards/extensions/components connected to it to expand functionality). The connection can be wired or wireless. The measuring device can also be of the Holter type—for signal recording lasting many hours, or stationary bedside.

Both stationary and portable devices can be battery powered, using disposable batteries, rechargeable batteries or other replaceable power supply sources. A stationary device can be operated using mains power supply. The devices can be equipped with wired interfaces for data uploading and downloading to and from devices (e.g. USB, SD cards, MMC memories, RJ45 network input) as well as with wireless ones (e.g., Wifi, Bluetooth, cellular modems). Both stationary and portable devices may have sockets for connecting test leads. The device allows for integration of wireless measuring devices instead of wired solutions.

Measuring impedance in an orthogonal system shows how resistance and reactance change over time during a cardiac contraction. When the heart is healthy, each beat in a rest measurement is similar to the previous one, and the time course of changes in the above parameters is cyclical. In the case of the heart affected by dilated heart disease, the tissue motion is reduced, which can result in reduced reactance and impedance changes. In left ventricular hypertrophy, changes in reactance and impedance can be more strongly expressed. An ECG measurement with the three conditions described above may indicate that the differences in recording may be difficult to notice. An ECG measurement in an orthogonal system, associated with an orthogonal impedance measurement system, allows for linking the stimulation in the form of voltage measured in the ECG to the change in tissue resistance in each of the measured directions. This is unique information because it shows the energy trajectory in a three-dimensional system, which is not available by any measurement method used so far. The excitation observed in the ECG is a control stimulation leading to contraction. A myocardial contraction results in a change of the resistance and reactance in the chest and has a hemodynamic effect. Until now, only the hemodynamic effect was observed, with no attention paid to what happens to resistance and reactance, and these quantities carry information about the time course of the contraction. Inefficient myocardium is not able to produce a significant hemodynamic effect (the essence of the failure is a low minute stroke volume), and still can produce a significant effect related to a change in chest resistance (strong motion of a pathologically hypertrophied myocardium). Supplementing the information by adding other sensors allowing for observation of the effects of cardiac contractions—including acoustic, vibration, ultrasonic measurement of signals from the heart moving in the chest, enables a more complete observation of the occurring phenomena and analysis of the dynamics of cardiac activity.

Example of Measurements for Healthy and Sick Patients

Figure 3:
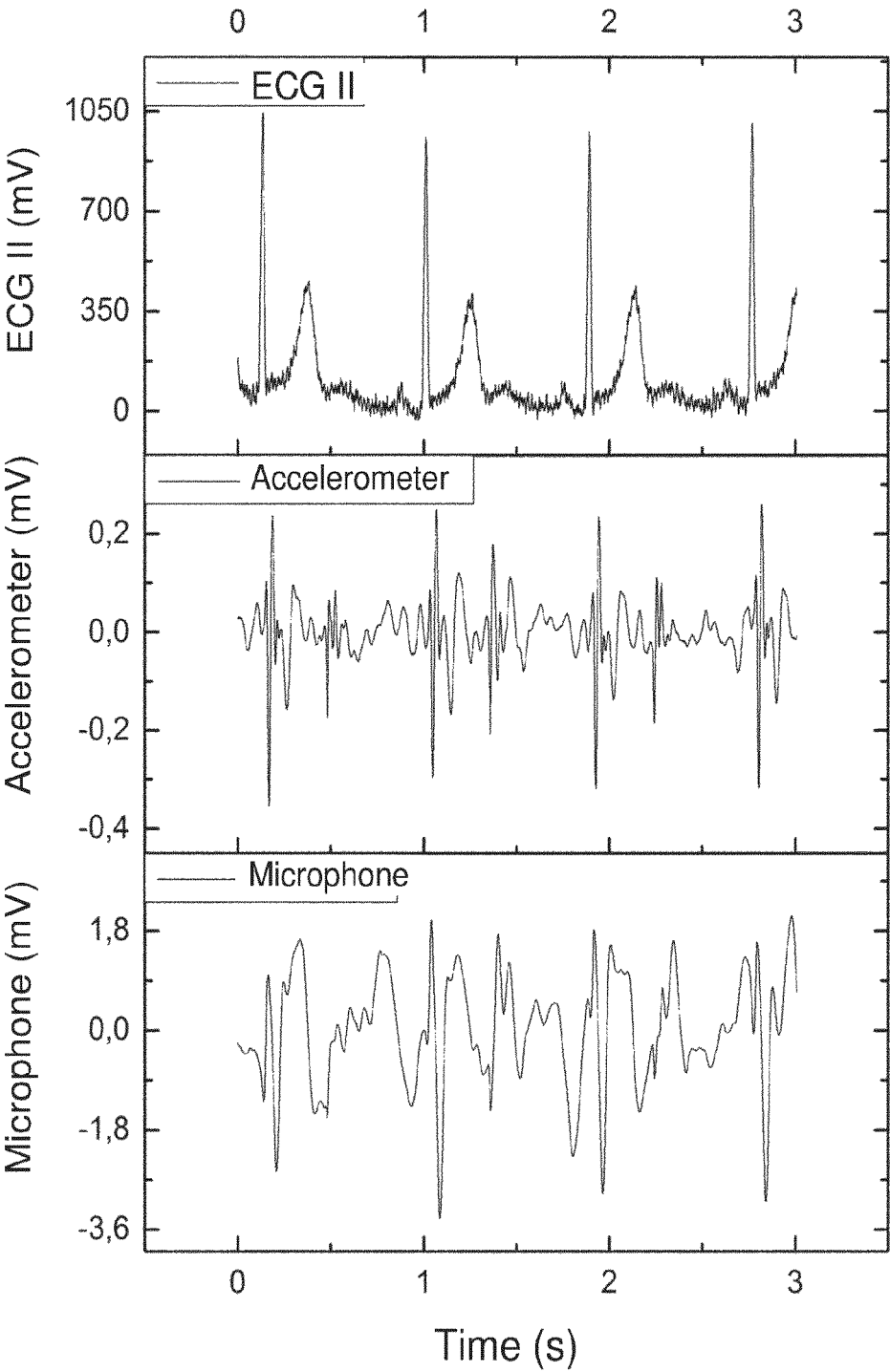
FIG. 3 shows the data obtained from measurements in a healthy subject.
Figure 4:
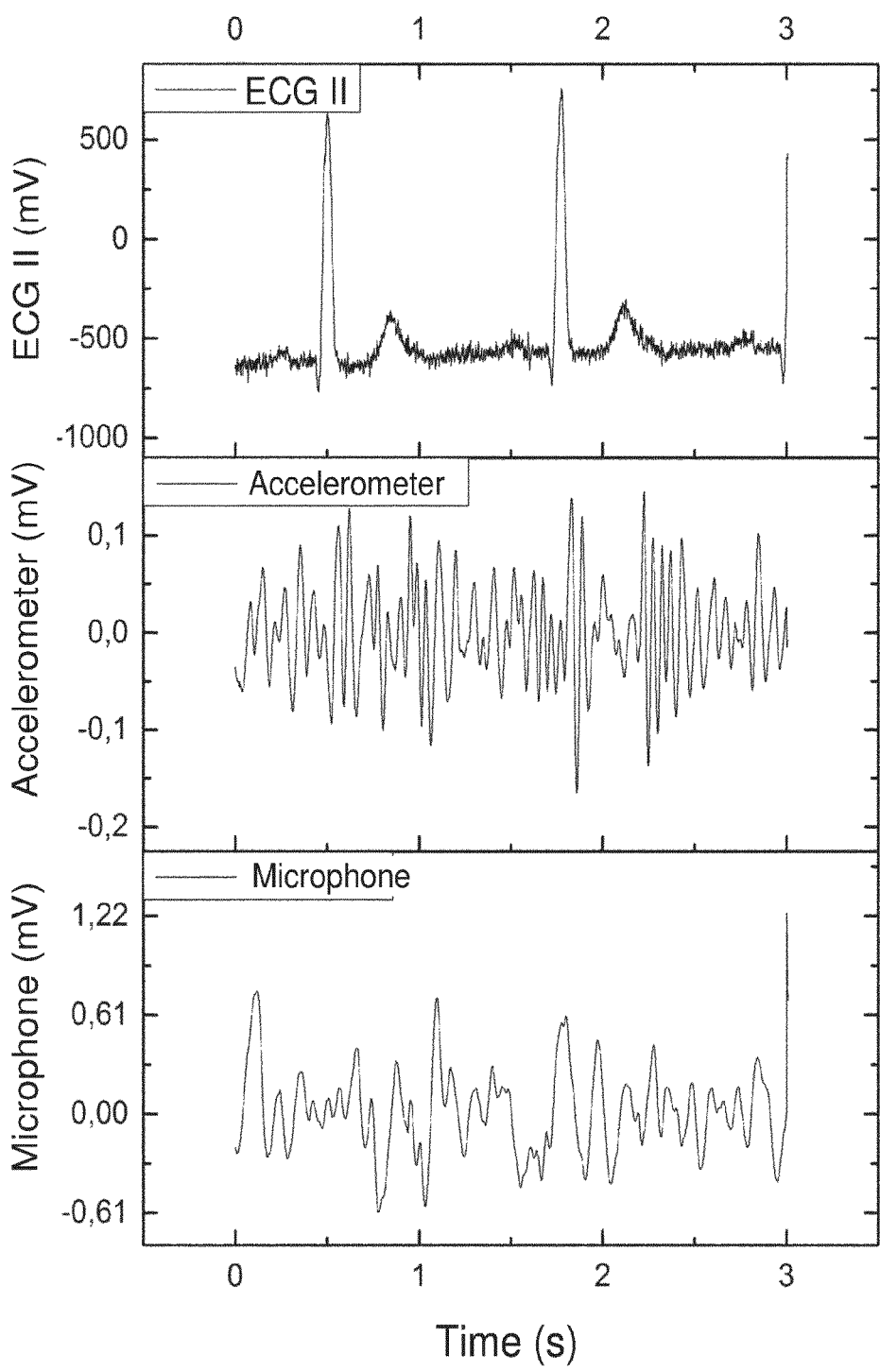
FIG. 4 shows the data obtained from measurements in a patient with cardiac disorders.

The patient had an ECG and a stethoscope and accelerometer were placed on the surface of the chest. The measurement was synchronous. In healthy subject, each heartbeat (observed on ECG) generated in the microphone and the accelerometer a signal waveform with a certain pattern (FIG. 3). The pattern was not observed in the sick person—the waveform seemed unrelated to the ECG signal (FIG. 4).

The analysis of the signal from the microphone collected during a 30 second measurement using analytical methods allowed to distinguish between the healthy and sick patients with 80% efficiency.

The invention claimed is:

1. A method for measuring multidimensional dynamics of cardiac activity, the method comprising simultaneously measuring:

three dimensional electrocardiogram (ECG) signals with a three dimensional ECG measurement system via a first set of electrodes configured for placement on a body of a subject, three dimensional impedance rheometry signals with an impedance rheometry system via a second set of electrodes configured for placement on the body of the subject, wherein the impedance rheometry signals measurement is performed for three orthogonal axes, and planes defined by the three orthogonal axes are configured to intersect a region of a heart of the subject, and tissue motion signals, wherein the tissue motion signals are measured with a sensor configured to be placed outside the body of the subject, the sensor being selected from among a membrane, an auscultation funnel, an accelerometer, a microphone, or a piezoelectric sensor, wherein the impedance rheometry signals measurement further comprises:

simultaneous generation of applied current of different frequencies for three orthogonal axes;

simultaneous impedance measurement for the same or other three orthogonal axes; and extracting real and imaginary parts of the impedance signals using signal processing hardware; and wherein the impedance rheometry signals measurement and the ECG signals measurement are carried out for the same three orthogonal axes;

wherein measurement data from the sensor, the first set of electrodes and the second set of electrodes are processed by a control system coupled to the three dimensional ECG measurement system and the impedance rheometry system, is the control system being configured to calculate parameters related to myocardium activity and integrate the measurement data into a multidimensional cardiac activity analysis.

2. The method according to claim 1, wherein one or more of the ECG measurement, the impedance rheometry measurement and the generation of applied current are carried out using electrodes in a Frank configuration or in a Leyko-Jamroży configuration, where:

a Z axis is determined by a first electrode configured to be located in a right supraclavicular fossa and a second electrode configured to be located in a position of a apex beat, a X axis is determined by a third electrode configured to be located at Erb's point and a fourth electrode configured to be located in a right posterior axillary line at its intersection with a line perpendicular to the Z axis and passing through the first electrode of the X axis, and a Y axis is determined by a fifth electrode configured to be located in a left posterior axillary line at a height of a third or fourth intercostal space and a sixth electrode configured to be disposed on a surface of the body at an exit point of a line passing through a first point of the Y axis and a point intersecting the X and Z axes.

3. The method according to claim 1, wherein the measurements are carried out using one time base.

4. A device for multidimensional analysis of the dynamics of cardiac activity, the device comprising:

a three dimensional electrocardiogram (ECG) measurement system comprising a first set of electrode configured to be disposed on a body of a subject for receiving three dimensional ECG signals;

a three dimensional impedance rheometry measurement system comprising:

an impedance measuring module;

a signal generator configured to generate applied currents of different frequencies for each orthogonal axis;

a second set of electrodes configured to be disposed on the body of the subject for receiving three dimensional impedance rheometry signals, wherein the impedance rheometry signals measurement is performed for three orthogonal axes, and planes defined by the three orthogonal axes are configured to intersect a region of a heart of the subject, at least one tissue motion sensor configured to be disposed outside of the body of the subject, the at least one tissue motion sensor being selected from one or more of a membrane sensor, an auscultation funnel, an accelerometer, a microphone piezoelectric sensor;

a hardware signal processor configured to process the measured data from the sensor, the first set of electrodes and the second set of electrodes simultaneously, extract real and imaginary components of the impedance, and compute multidimensional cardiac activity parameters including physical currents, energy, and work; and a time-synchronized controller module providing a common time base for all measurements.

5. The device according to claim 4, wherein the device comprises an interface for data transfer.

6. The device according to claim 4, wherein the device comprises a pulse oximetry device with PTT measurement; and wherein the hardware signal processor is configured to integrate PTT data with the multidimensional cardiac activity analysis.

7. The device according to claim 4, further comprising a data interface configured to transmit the processed cardiac dynamics data to an external system.

\* \* \* \* \*